US005424335A

United States Patent [19]
Abbott

[11] Patent Number: 5,424,335
[45] Date of Patent: Jun. 13, 1995

[54] METHANOL SYNTHESIS

[75] Inventor: Peter E. J. Abbott, Cleveland, England

[73] Assignee: Imperial Chemical Industries PLC, London, England

[21] Appl. No.: 155,761

[22] Filed: Nov. 23, 1993

[51] Int. Cl.$^6$ ............................................. C07C 29/151
[52] U.S. Cl. ...................................... 518/706; 518/707
[58] Field of Search ................................. 518/706, 707

[56] References Cited

U.S. PATENT DOCUMENTS 3,615,200 10/1971 Konoki .
4,226,795 10/1980 Bowman .
4,407,973 10/1983 Van Dijk et al. .
4,778,662 10/1988 Pinto .

FOREIGN PATENT DOCUMENTS 102380 3/1993 Romania .
1259945 1/1972 United Kingdom .
2233329 1/1991 United Kingdom .

OTHER PUBLICATIONS

Derwent Abstract of RO 102380 Feb. 1989.
PEJ Abbott: "Methanol Reactor Design Choices", paper presented at the 1992 World Methanol Conference, Monte Carlo, Monaco on Dec. 8–10, 1992.

*Primary Examiner*—Howard T. Mars
*Attorney, Agent, or Firm*—Cushman Darby & Cushman

[57] ABSTRACT

The purge gas from a methanol synthesis loop is subjected to a further step of methanol synthesis, preferably while in indirect heat exchange with the purge gas undergoing heating to the synthesis inlet temperature so that the reacted purge gas, containing synthesized methanol, leaves the synthesis catalyst at a temperature below the maximum temperature achieved by the reacting purge gas during passage over the catalyst.

The synthesis loop can be operated less efficiently, eg at a lower pressure or with added carbon dioxide, than is conventional since the additional methanol produced from the purge gas compensates for the loss of loop efficiency.

The addition of the purge gas synthesis stage enables existing plants to be uprated by lowering the loop pressure, thus enabling a greater throughput through the synthesis gas compressor to be achieved.

3 Claims, 2 Drawing Sheets

METHANOL SYNTHESIS

This invention relates to methanol synthesis, and in particular to a methanol synthesis process utilising a synthesis loop wherein fresh methanol synthesis gas containing hydrogen and carbon oxides is compressed, eg to a pressure within the range 40–150 bar abs., then mixed with recycle gas, the mixture is heated and passed over a methanol synthesis catalyst, the reacted gas containing synthesised methanol is cooled, synthesised methanol is then separated to leave unreacted gas, part of which is discharged as a purge stream while the reminder is recycled as the aforesaid recycle gas.

BACKGROUND TO THE INVENTION

In a process of the above nature, the purge stream is taken from the loop in order to prevent a build up of inert components, eg methane and often also nitrogen, in the loop. Also, where the fresh methanol synthesis gas has an excess of one of the reactants over that required for methanol synthesis according to the equations $$2H_2 + CO \rightarrow CH_3OH$$

$$3H_2 + CO_2 \rightarrow CH_3OH + H_2O$$

the purge serves to remove that excess and so prevent a build-up of unreacted reactant in the synthesis loop. In many plants, hydrogen is present in an excess.

Inevitably the purge will contain, in addition to the inert components, some hydrogen and carbon oxides. While the purge can be used as fuel, eg to provide some or all of the heat required in reforming processes used to make the fresh synthesis gas, this represents a degradation or waste of some valuable components. Thus where the fresh methanol synthesis gas is hydrogen-rich, ie contains an excess of hydrogen over that required for reaction with the carbon oxides present, and as is often the case where the fresh methanol synthesis gas is derived from a feedstock such as natural gas, the purge will inevitably contain some carbon oxides and so these will be wasted.

By careful selection of the operating conditions, eg catalyst volume, synthesis temperature, purge rate, inerts content, a commercial methanol plant operating at a synthesis pressure of 100 bar abs., typically has a carbon efficiency of the order of 93–98%, ie 93–98% by weight of the carbon present in the fresh synthesis gas as carbon oxides is converted to methanol. At lower synthesis pressures the carbon efficiency is liable to be somewhat lower.

In the present invention, further methanol is produced by subjecting the purge gas to a further methanol synthesis step. Also by operating the synthesis loop at a reduced pressure an increase in throughput can be achieved without an increase in the compression power requirements. Also by effecting the further stage of methanol synthesis under conditions wherein the gas is cooled, while it is undergoing the further synthesis reaction, by indirect heat exchange with the gas being supplied to the further synthesis step, efficient operation may be achieved. As a result the carbon efficiency may be increased, and/or other advantages as will be described hereinafter may be achieved.

PRIOR ART

U.S. Pat. No. 4,226,795 and U.S. Pat. No. 4,407,973 disclose processes wherein the composition of the purge from a methanol synthesis loop is modified by adding components such as carbon oxides or fresh methanol synthesis gas, and then the modified purge gas is subjected to a further stage of methanol synthesis. In the present invention no such modification of the purge gas composition is effected prior to the further methanol synthesis step.

U.S. Pat. No. 3,615,200 describes a process wherein the purge from an ammonia or methanol synthesis loop is compressed to a higher pressure than was employed in the synthesis loop and then this compressed purge is subjected to a further synthesis step, either on a "once-through" basis or in a second synthesis loop. The power required for the additional compression may be recovered from the purge from the second loop or, in the "once-through" process, from the gas after separation of the product synthesised in the further synthesis step.

GB 1259945 describes a process wherein the purge from a methanol synthesis loop is subjected to a further synthesis step, preferably in a second synthesis loop. In the example of this reference a quench reactor, containing a volume of catalyst that was about 97% of that employed in the first synthesis loop, was used to effect methanol synthesis from the first loop purge in a second loop.

RO 102380 (Derwent WPI 93-173409/21) describes a process wherein the purge gas from a methanol synthesis loop is subjected to a non-circulatory, ie "once through", further methanol synthesis in one or more radial flow isothermal reactors at a lower temperature and pressure than in the aforesaid loop.

U.S. Pat. No. 4,778,662 describes a reactor for ammonia or methanol synthesis wherein the gas undergoing the synthesis reaction is cooled by indirect heat exchange with the gas being supplied to that synthesis reaction.

GENERAL DESCRIPTION OF THE INVENTION

One embodiment of the present invention provides an improvement in a process for the production of methanol wherein fresh methanol synthesis gas containing hydrogen, carbon oxides, and inert gases is compressed to an elevated synthesis pressure and fed to a synthesis loop wherein the fresh synthesis gas is mixed with recycle gas, the mixture of compressed synthesis gas and recycle gas is heated and passed over a methanol synthesis catalyst to forming a reacted gas stream containing methanol and unreacted gases, the reacted gas stream is cooled to below the dew point of methanol so as to condense methanol which is separated from the reacted gas stream to leave a stream of residual gas, part of which is recycled as the aforesaid recycle gas, and the reminder is discharged from the loop as a purge gas;

said improvement comprising subjecting the purge gas to a further step of methanol synthesis by heating said purge gas to a synthesis inlet temperature, synthesising methanol from said heated purge gas by passing it over a methanol synthesis catalyst while in indirect heat exchange with said purge gas undergoing heating to said synthesis inlet temperature, whereby heat is transferred from the purge gas undergoing synthesis to that being heated to the synthesis inlet temperature whereby the purge gas, containing synthesised methanol, leaves the catalyst at a temperature below the maximum temperature achieved by said reacting purge gas during passage over said catalyst, cooling the reacted puree gas to below the dew point of the methanol therein so as to condense said methanol, separating the condensed methanol and discharging the reminder of the reacted purge gas.

In the present invention the purge gas is thus subjected to a "once-through" methanol synthesis: since the volume of the purge gas discharged from the synthesis loop and treated in the aforesaid further synthesis step is only a small fraction, typically 10–30%, of the volume of the fresh synthesis gas fed to the synthesis loop, the volume of catalyst required in the further synthesis stage is small, typically 5–15%, particularly 5–10%, of that used in the synthesis loop. Consequently the size of the synthesis reactor employed in the further synthesis stage is relatively small.

As indicated above, in this embodiment of the invention, the further synthesis step is effected under conditions of indirect heat exchange, eg using a reactor of the type disclosed in the aforesaid U.S. Pat. No. 4,778,662. This enables the exit temperature to be below, eg 5° C. to 50° C. below, the maximum temperature achieved by the gas undergoing reaction in the further synthesis stage, and enables a higher conversion to be achieved.

Usually it is desirable to recover heat from the gas leaving a methanol synthesis catalyst: while this heat recovery often includes heating the feed to the methanol synthesis step, it is usually desirable to recover high grade heat, eg by steam raising, and so a high exit temperature is desirable. Hence the efficiency with which the synthesis step is conducted represents a compromise between the desirability of obtaining a high conversion to methanol, which is favoured by low temperatures, and a high exit temperature in order to obtain high grade heat recovery. For this reason, as described in the aforesaid U.S. Pat. No. 4,778,662 the synthesis reactor often contains an adiabatic catalyst bed, ie a bed that does not have any heat exchange means therein, downstream of the heat exchange portion. However, in the present invention, since the purge gas is treated in a "once-through" system, the volume thereof is small and so the amount of heat that could be recovered is small. Consequently, in the present invention, it is more economic to operate the further synthesis stage with a low exit temperature than attempt to recover high grade heat. Therefore it is preferred that the reactor employed for the further synthesis stage does not have an adiabatic bed of catalyst downstream of the bed having the heat exchange provision. The exit temperature from the further synthesis step may therefore be significantly lower than in systems where this type of reactor is employed in a circulatory system, eg in a synthesis loop.

In the present invention heat may be recovered from the reacted purge gas leaving the synthesis catalyst by heat exchange with the feed to the further synthesis step, ie a stage of feed/effluent heat exchange.

In the present invention, using the type of reactor wherein there is heat exchange between the gas undergoing synthesis and the gas being fed to the catalyst bed has advantages over the conventional "quench" type of reactor wherein one or more "shots" of cold synthesis gas are injected into the into the catalyst bed, or between beds (where a multibed reactor is used) in order to reduce the temperature of the gas undergoing reaction. Thus it is possible, using the aforesaid heat exchange type of reactor, to operate at significantly lower exit temperatures. This is important when consideration is made of the decline in activity of a methanol synthesis catalyst with time when the achievable approach to equilibrium increases from a relatively low figure, eg 10° C., with fresh catalyst to a high value, eg 37° C. that is typical of a catalyst nearing the end of its useful life. High, eg 37° C., approach to equilibrium conditions may also occur when a significant proportion of carbon oxides is discharged from the loop in the purge stream. The following table illustrates typical temperatures, and once-through carbon efficiency for the heat exchange reactor and a quench reactor for low and high approach conditions.

| Equilibrium Approach (°C.) | Reactor | Exit temp (°C.) | Carbon efficiency (%) |
|---|---|---|---|
| 10 | Heat exchange | 210 | 89 |
| 10 | Quench | 250 | 70 |
| 37 | Heat exchange | 229 | 62 |
| 37 | Quench | 265 | 35 |

It is seen from this table that there is a significant advantage in using a heat exchange reactor compared to a quench reactor whether high or low approaches to equilibrium are achieved.

It would be possible to achieve a low exit temperature with an adiabatic bed followed by an isothermal section, ie where the temperature was maintained constant by means of heat exchange with a coolant such as boiling water (thus raising steam), but the resulting steam pressure would be relatively low and so not very useful and the system would be more complex and difficult to integrate into an existing plant.

The present invention is particularly applicable to plants where the maximum loop pressure is in the range 40 to 150 bar abs.

In many methanol plants, one constraint upon the plant capacity is the step of compressing the fresh methanol synthesis gas to the desired synthesis pressure. Thus if the plant is designed to operate with a synthesis pressure of, for example, 100 bar abs., the fresh synthesis gas compressor is capable of compressing only a certain amount of fresh synthesis gas to this pressure; however other parts of the plant may be capable of handling significantly greater amounts of gas. In such cases the present invention enables an existing plant to be uprated. Thus, since further methanol is synthesised from the loop purge, it may be desirable to operate the synthesis loop in a less efficient manner. For example, the loop can be operated at a lower pressure: the synthesis gas compressor will normally be able to compress a greater amount of synthesis gas if the delivery pressure is decreased.

Accordingly a second embodiment of the invention provides a method of uprating a methanol synthesis plant, wherein fresh methanol synthesis gas containing hydrogen, carbon oxides, and inert gases is compressed to an elevated synthesis pressure and fed to a synthesis loop wherein the fresh synthesis gas is mixed with recycle gas, the mixture of compressed synthesis gas and recycle gas is heated and passed over a methanol synthesis catalyst to form a reacted gas stream containing methanol and unreacted gases, the reacted gas stream is cooled to below the dew point of methanol so as to condense methanol which is separated from the reacted gas stream to leave a stream of residual gas, part of which is recycled as the aforesaid recycle gas, and the remainder is discharged from the loop as a purge gas;

said method comprising decreasing the delivery pressure of the fresh synthesis gas compressor and increasing the rate at which the fresh synthesis gas is supplied to the synthesis loop without increasing the compression power required, and subjecting the purge gas to a further step of methanol synthesis by heating said purge gas to a synthesis inlet temperature, synthesising methanol from said heated purge gas by passing it over a methanol synthesis catalyst, cooling the reacted purge gas to below the dew point of the methanol therein so as to condense said methanol, separating the condensed methanol and discharging the remainder of the reacted purge gas.

The synthesis reactor employed in this second embodiment for effecting the synthesis of methanol from the purge gas may be of the aforesaid type wherein there is indirect heat exchange of the gas undergoing the synthesis reaction with the purge gas undergoing heating to said synthesis inlet temperature, whereby heat is transferred from the purge gas undergoing synthesis to that being heated to the synthesis inlet temperature whereby the purge gas, containing synthesised methanol, leaves the catalyst at a temperature below the maximum temperature achieved by said reacting purge gas during passage over said catalyst. While such a reactor is preferably employed, as a result of the significant benefits that may accrue from decreasing the loop pressure, eg the increase in throughput without increasing the compression power, other forms of reactor, eg quench reactors or isothermal reactors, optionally with an initial adiabatic bed, may be employed.

Preferably in this second embodiment of the invention, the delivery pressure of the fresh synthesis gas compressor is decreased by about 10–25%, typically by 15–25 bar abs., for example from 100 bar abs. to 80 bar abs., thereby enabling the throughput of the compressor to be increased significantly without an increase in the power required for that compression.

Although the synthesis loop is liable to be less efficient at the lower synthesis pressure, the production of the additional methanol from the purge can restore the overall efficiency thus enabling the capacity of the plant to be increased, simply by adding a relatively small heat exchange reactor containing methanol synthesis catalyst, heat exchangers to heat the purge to the desired inlet temperature and to cool the reacted purge gas, and a catchpot to effect separation of the methanol synthesised from the purge gas. In this mode of operation, it may also be desirable to alter the synthesis temperature in the synthesis loop and/or to increase the proportion of the residual gas taken as a puree. Since the volume of puree treated is only a small proportion of the fresh synthesis gas fed to the synthesis loop, in some cases it may be desirable to incorporate a small compressor to increase the pressure of the puree prior to methanol synthesis therefrom. The degree of compression of the puree may be such that the pressure at which the methanol synthesis from the puree is effected is above, equal to, or below the synthesis pressure of the loop in the unmodified plant. Power required for this further compression may in some cases be obtained by letting down the pressure of the reacted puree gas remaining after separation of the condensed methanol therefrom in a turbine driving the purge gas compressor. Alternatively, since less power may be required for effecting circulation of the gas round the synthesis loop, this power saving may be employed for compression of the puree prior to the puree gas synthesis step.

This method of uprating a plant, ie by decreasing the loop synthesis pressure, will generally not be desirable when the loop pressure of the existing plant is relatively low, eg below 70 bar abs., since the rate at which the efficiency of loops operating at lower pressures falls with decreasing pressure is too great for the puree gas treatment to be advantageous. Thus at a low loop pressure, the loop efficiency is relatively poor which imposes a significant burden on the puree gas treatment stage even without a further decrease in the loop pressure. However, the adoption of the first embodiment of the invention, namely a puree gas synthesis stage operating under heat exchange conditions as aforesaid, in a plant operating at low pressures is advantageous even if the loop pressure is not decreased.

Where, as is often the case, the fresh synthesis gas is hydrogen rich, it may be possible to uprate an existing plant by adding carbon dioxide from a suitable source to the synthesis loop. The amount of carbon dioxide added is preferably sufficient that the gas entering the loop synthesis catalyst is no longer hydrogen-rich: indeed it is preferred to add sufficient carbon dioxide that the ratio of the difference between the molar proportions of hydrogen and carbon dioxide to the sum of the molar proportions of carbon oxides present is in the range 1.8 to 2.0. Although the carbon efficiency of the loop may drop as a result of such carbon dioxide addition, again the overall carbon efficiency may be improved as well as increasing the amount of methanol produced.

It will be appreciated that both the above techniques for increasing the capacity of a plant may be adopted: thus in addition to decreasing the loop synthesis pressure, imported carbon dioxide may be added.

In another alternative where the circulator is the limiting factor, an existing plant may be uprated by increasing both the amount of fresh feed to the loop and the purge rate from the loop, possibly together with a decrease in the loop pressure: this enables the throughput to be increased without increasing the circulator power requirement. This may also have a beneficial effect on methanol production in the loop as it may enable the inerts content of the loop to be decreased.

Increasing the loop purge rate, with consequential treatment of the purge to synthesise methanol therefrom, without increasing the fresh synthesis gas feed rate and/or without decreasing the loop pressure may also be advantageous as this enables the loop circulation rate to be decreased, thus giving a saving in circulator power requirements.

In some cases, where there are a number of plants at a single location, it may be advantageous to utilise a common purge gas treatment facility, eg by combining the purge streams from two or more plants and treat the combined purge in a single synthesis reactor.

Both the loop synthesis step and the purge gas synthesis step may be operated using conventional methanol synthesis catalysts, eg copper/zinc oxide/alumina compositions, and temperatures within the conventional ranges: thus the catalyst inlet temperatures are preferably within the range 210° to 250° C. and the exit temperatures are preferably within the range 210° to 280° C., although as indicated above, the exit temperature from the loop purge synthesis step may be somewhat lower than is usual. The space velocity in each synthesis step may be in the conventional range, eg 5000–20000 $Nm^3/h$ per $m^3$ of catalyst. In the heat exchange reactor, the area of the heat exchange surfaces is typically in the range 5 to 20 $m^2$ per $m^3$ of catalyst.

BRIEF DESCRIPTION OF THE DRAWINGS

The invention is illustrated by reference to the accompanying drawings wherein.

DESCRIPTION OF SPECIFIC EMBODIMENT

Figure 1:
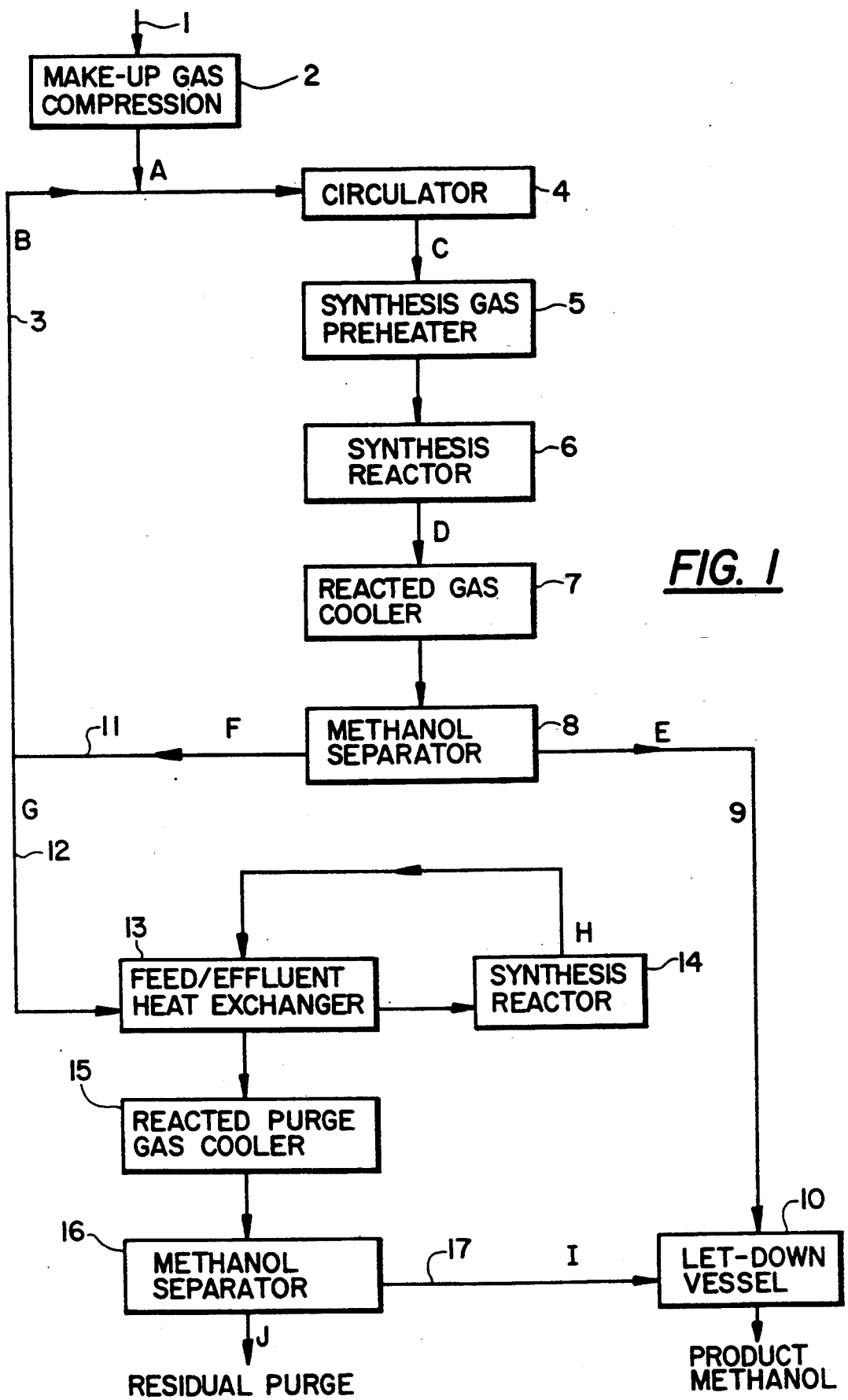
FIG. 1 is a diagramatic flowsheet.

Referring to FIG. 1, fresh synthesis gas, comprising hydrogen, carbon monoxide, carbon dioxide, and a small proportion of methane and nitrogen, typically at a pressure of about 15 bar abs., is fed via line 1 to a make-up gas compressor 2 where it is compressed to the methanol loop recycle pressure, typically about 100 bar abs. The compressed fresh synthesis gas (stream A) is mixed with recycle gas (stream B) supplied via line 3 and the mixture is fed to a circulator 4 which serves to increase the pressure to the maximum loop pressure. The compressed mixture (stream C) from circulator 4 is then fed to a preheater 5 where it is heated to the desired synthesis inlet temperature, typically 240° C. The heated gas is then fed to the synthesis reactor 6 where it contacts the synthesis catalyst, typically pellets of a copper/zinc oxide/alumina composition. The reacted gas (stream D) is then fed to a cooler 7 where heat is recovered and the reacted gas cooled to below the dew pointy of methanol. Typically it is cooled to a temperature of the order of 40° C. Methanol condenses and is then separated from the cooled reacted gas in a separator 8. The methanol, which will contain a small proportion of water and dissolved gases, is discharged via line 9 (stream E) to a pressure let down vessel 10. The residual gas (stream F) leaves the separator 8 via line 11. Part of this residual gas is recycled via line 3, while the remainder is discharged via line 12 as a purge (stream G).

The purge stream G typically is about 25% of the compressed fresh make-up gas A and the recycle gas B is typically about 3-5 times the amount of the compressed make-up gas A.

In the present invention stream G is preheated, eg in a feed/effluent heat exchanger 13, to a temperature typically in the range 75°-200° C. and then fed to a synthesis reactor 14. In this synthesis reactor, the gas is further heated to a catalyst inlet temperature, typically of the order of 210°-250° C. by indirect heat exchange with the gas undergoing reaction in the synthesis reactor 14, and then passes through a bed of catalyst, typically pellets of a copper/zinc oxide/alumina composition. As it passes through the bed of catalyst, methanol synthesis occurs and heat is evolved. The gas temperature rises as the gas passes through the bed of catalyst. However, since there is indirect heat exchange with the purge gas being fed to the catalyst, heat is transferred from the reacting gas to the gas being fed to the catalyst. As a consequence, the temperature at which the reacted gas (stream H) leaves the catalyst bed is typically in the range 210°-280° C., typically up to 50° C. below the maximum temperature achieved in the catalyst bed.

The reacted gas (stream H) leaving the synthesis reactor 14 is then used as the heating medium in the feed/effluent heat exchanger 13 and then is cooled further, in heat exchanger 15, to below the dew point of methanol. The methanol in the reacted purge gas is thus condensed and is separated in separator 16. The separated methanol (stream I) is discharged via line 17 to the pressure let down vessel 10, while the remaining gas (stream J) is discharged, eg for use as fuel.

Figure 2:
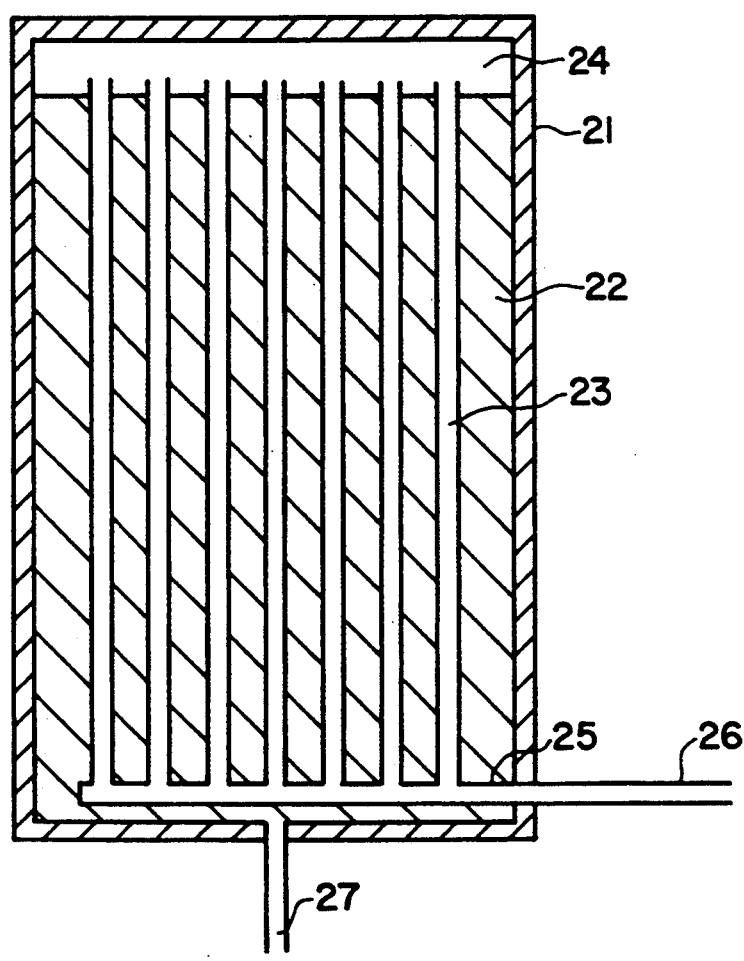
FIG. 2 is a diagramatic section through the synthesis reactor employed to treat the purge gas.

A suitable form of reactor for use as the synthesis reactor 14 is shown in FIG. 2. The reactor comprises an outer pressure vessel 21 provided with a single bed 22 of catalyst particles. A plurality of vertical tubes 23 are disposed in the catalyst bed and open at their upper ends into the space 24 above the catalyst bed 22. The tubes 23 extend from a header pipe 25 to which the pre-heated purge gas is fed via line 26. The vessel is provided with an outlet port 27 for the reacted gas. It is seen that as the puree gas fed via header 25 passes up the tubes 23, heat exchange can take place across the walls of the tubes 23 with the reacting gas passing down through the catalyst bed 22 from the space 24 above the bed to the outlet port 27.

Since the reacted purge gas is not recycled, it is possible to operate the puree gas synthesis stage with a significant pressure drop in the catalyst bed without incurring any significant penalty. Accordingly it is possible to use a smaller particle size catalyst, and so obtain a greater activity per unit catalyst bed volume than would be conventional, and/or to use a relatively high aspect ratio catalyst bed, ie a bed that is relatively long in relation to its cross sectional area.

The invention is illustrated by the following calculated examples, which all assume that a commercially available copper/zinc oxide/alumina methanol synthesis catalyst is employed.

EXAMPLE 1 (COMPARATIVE)

In this example the flowsheet of FIG. 1 is employed with the omission of items 13-17. Thus there is no treatment of the purge gas. The pressure P (bar abs.), temperature T (°C.) and flow rates (kmol/h, rounded to the nearest integer) of the components of the various streams are shown in Table 1.

TABLE 1

| Stream | T (°C.) | P (bar) | Flow rate (kmol/h) | | | | | |
|---|---|---|---|---|---|---|---|---|
| | | | $H_2$ | $CO_2$ | CO | $H_2O$ | $CH_3OH$ | $CH_4 + N_2$ |
| A | 40 | 99 | 8705 | 877 | 1813 | 0 | 0 | 304 |
| B | 40 | 99 | 47159 | 552 | 551 | 28 | 259 | 5154 |
| C | 100 | 106 | 55864 | 1430 | 2364 | 28 | 259 | 5458 |
| D | 270 | 102 | 49794 | 595 | 582 | 863 | 2876 | 5458 |
| E | 40 | 99 | 14 | 12 | 1 | 834 | 2603 | 17 |
| F | 40 | 99 | 49780 | 583 | 582 | 29 | 273 | 5441 |
| G | 40 | 99 | 2621 | 31 | 31 | 2 | 14 | 287 |

If the fresh synthesis gas is supplied to the compressor 2 at a pressure of 16.2 bar abs., the power required for the compressor 2 is 24.5 MW while that required for the circulator is 4.55 MW. The amount of methanol in the product stream E corresponds to about 2000 te/d (metric tons per day). The carbon efficiency (ie moles of methanol produced/moles of carbon oxides in the fresh synthesis gas) is 96.8%.

EXAMPLE 2

In this example, the flowsheet of FIG. 1 is used, using a fresh synthesis gas having the same composition as in Example 1. The synthesis reactor 14 is of the type shown in FIG. 2. The loop pressure is lower than in Example 1 so that the compressor 2 could have a higher throughput without an increase in its power requirements. The pressure P (bar abs.), temperature T (°C.) and flow rates (kmol/h, rounded to the nearest integer) of the components of the various streams are shown in Table 2. The purge gas is heated to 150° C. in heat exchanger 13, ie prior to entering the heat exchange tubes of reactor 14.

TABLE 2

| Stream | T (°C.) | P (bar) | $H_2$ | $CO_2$ | CO | $H_2O$ | $CH_3OH$ | $CH_4 + N_2$ |
|---|---|---|---|---|---|---|---|---|
| A | 40 | 82.5 | 9151 | 923 | 1906 | 0 | 0 | 320 |
| B | 40 | 82.5 | 36228 | 1112 | 996 | 25 | 239 | 3589 |
| C | 100 | 88.3 | 45380 | 2035 | 2902 | 25 | 239 | 3908 |
| D | 275 | 84.0 | 39333 | 1233 | 1083 | 827 | 2861 | 3908 |
| E | 40 | 82.5 | 12 | 25 | 2 | 800 | 2602 | 13 |
| F | 40 | 82.5 | 39321 | 1207 | 1081 | 27 | 259 | 3895 |
| G | 40 | 82.0 | 3093 | 95 | 85 | 2 | 20 | 306 |
| H | 229 | 79.0 | 2822 | 45 | 25 | 52 | 131 | 306 |
| I | 40 | 77.0 | 1 | 1 | 0 | 50 | 114 | 0 |
| J | 40 | 77.0 | 2821 | 44 | 25 | 2 | 17 | 306 |

The peak temperature attained by the reacting gas in reactor 14 is 269° C., ie 40° C. above the synthesis exit temperature. Assuming that the fresh synthesis gas is supplied at a pressure of 16.2 bar abs, despite the increased fresh synthesis gas feed rate, the power requirement for compressor 2 is reduced to 22.8 MW. Furthermore, it is seen that the amount of recycle (stream B) is significantly decreased compared to Example 1 so that, despite the increased throughput from the compressor 2, the power requirement for the circulator is decreased to 4.1 MW. The amount of methanol in the product streams E and I corresponds to about 2088 te/d (metric tons per day), ie an increase of about 4.42% over Example 1. The carbon efficiency is 96.0% despite the operation at a significantly lower loop pressure.

It is further noted that the provision of the treatment of the loop purge (ie stream G) enables the loop inerts level to be decreased (eg the inerts content of stream D is decreased from 9.1% to 7.9%) and the loop to be operated at a higher carbon oxides content.

EXAMPLE 3

In this example there is shown the benefit that can be achieved by the use of a heat exchange reactor to synthesise methanol from the purge gas from a low pressure (55 bar abs.) loop. The heat exchange reactor, of the type shown in FIG. 2, used to treat the purge gas contains 4 m³ of methanol synthesis catalyst and the surface area of the tubes immersed in the catalyst is 8.9 m² per m³ of catalyst. The pressure P (bar abs.), temperature T (°C.) and flow rates (kmol/h, rounded to the nearest integer) of the components of the various streams are shown in Table 3. The purge gas is heated to 190° C. in heat exchanger 13, ie prior to entering the heat exchange tubes of reactor 14.

TABLE 3

| Stream | T (°C.) | P (bar) | $H_2$ | $CO_2$ | CO | $H_2O$ | $CH_3OH$ | $CH_4 + N_2$ |
|---|---|---|---|---|---|---|---|---|
| G | 43 | 55 | 1318 | 105 | 91 | 1 | 9 | 225 |
| H | 270 | 53.5 | 1180 | 79 | 61 | 27 | 65 | 225 |
| I | 40 | 52 | 0 | 1 | 0 | 26 | 56 | 0 |
| J | 40 | 52 | 1180 | 78 | 61 | 1 | 10 | 225 |

The peak temperature attained by the reacting gas is 276° C., ie 6° C. above the synthesis exit temperature. The methanol in stream I corresponds to 42.7 te/d, and the carbon efficiency in the purge gas treatment stage is 28.6%.

EXAMPLE 4

In this example a two bed quench reactor is employed in place of the heat exchange reactor of Example 3, with 2 m³ of catalyst in the first bed and 4 m³ of catalyst in the second bed under conditions giving a similar exit temperature to that of Example 3. The purge gas has essentially the same composition as in Example 3, but 76% by volume of the purge gas is heated to a catalyst inlet temperature of 240° C. in a feed/effluent heat exchanger analagous to heat exchanger 13 of FIG. 1 and fed to the first catalyst bed of the quench reactor, while the remaining 24% is added to the reactor at 43° C. as the "cold" quench between the first and second beds. The pressure P (bar abs.), temperature T (°C.) and flow rates (kmol/h, rounded to the nearest integer) of the components of the various streams are shown in Table 4.

TABLE 4

| Stream | T (°C.) | P (bar) | $H_2$ | $CO_2$ | CO | $H_2O$ | $CH_3OH$ | $CH_4 + N_2$ |
|---|---|---|---|---|---|---|---|---|
| G | 43 | 55 | 1325 | 105 | 92 | 1 | 9 | 226 |
| H | 273 | 53.2 | 1189 | 80 | 61 | 26 | 55 | 226 |
| I | 44 | 52 | 0 | 1 | 0 | 24 | 44 | 0 |
| J | 44 | 52 | 1189 | 80 | 61 | 2 | 12 | 226 |

The peak temperature attained by the reacting gas is 279° C. at the exit of the first bed. On addition of the quench gas the temperature falls and thereafter gradually rises to the second bed exit temperature of 273° C. The amount of methanol in stream I corresponds to about 28.8 te/d of methanol. By comparison with Example 3 it is seen that less methanol is produced, despite the use of 50% more catalyst. Using a smaller amount of catalyst would give a decreased amount of methanol.

EXAMPLE 5

In this example the use of a heat exchange reactor of the type shown in FIG. 2 containing about 2.5 m$^3$ of methanol synthesis catalyst is employed to synthesise methanol from the purge of a synthesis loop operating at about 100 bar abs. on a hydrogen-rich fresh feed gas. The pressure P (bar abs.), temperature T (°C.) and flow rates (kmol/h, rounded to the nearest integer) of the components of the various streams of the purge treatment stage are shown in Table 5. The purge gas was heated to 148° C. in heat exchanger 13, ie prior to entering the heat exchange tubes of reactor 14.

TABLE 5

| Stream | T (°C.) | P (bar) | Flow rate (kmol/h) | | | | | |
|---|---|---|---|---|---|---|---|---|
| | | | H$_2$ | CO$_2$ | CO | H$_2$O | CH$_3$OH | CH$_4$ + N$_2$ |
| G | 37 | 99.8 | 1090 | 26 | 36 | 0 | 4 | 153 |
| H | 250 | 96.8 | 972 | 8 | 5 | 19 | 54 | 153 |
| I | 40 | 95 | 0 | 0 | 0 | 19 | 49 | 1 |
| J | 40 | 95 | 971 | 8 | 5 | 1 | 5 | 153 |

The peak temperature attained by the reacting gas is 272° C., ie 22° C. above the exit temperature. The methanol flow rate in stream I corresponds to about 37.8 te/d. The carbon efficiency in the purge gas treatment stage is 78.7%.

EXAMPLE 6

By addition of carbon dioxide to the fresh synthesis gas fed to the synthesis loop producing the purge gas of Example 5, not only can more methanol be produced in the loop synthesis reactor, but also a smaller purge can be taken therefrom. The purge gas from the loop will also have a modified composition. By treatment of this purge in a heat exchange reactor of the type shown in FIG. 2, with the purge gas being heated to only 80° C. in the heat exchanger 13, a significantly greater amount of methanol can also be produced from the loop purge. The pressure P (bar abs.), temperature T (°C.) and flow rates (kmol/h, rounded to the nearest integer) of the components of the various streams of the purge gas treatment stage are shown in Table 6. The purge stream G in this table is the purge resulting from the addition of carbon dioxide to the fresh synthesis gas fed to the synthesis loop producing the purge stream G of Example 5, and, as in Example 5, the purge synthesis reactor contains 2.5 m$^3$ of catalyst.

TABLE 6

| Stream | T (°C.) | P (bar) | Flow rate (kmol/h) | | | | | |
|---|---|---|---|---|---|---|---|---|
| | | | H$_2$ | CO$_2$ | CO | H$_2$O | CH$_3$OH | CH$_4$ + N$_2$ |
| G | 37 | 99.8 | 764 | 51 | 45 | 0 | 3 | 150 |
| H | 240 | 96.8 | 615 | 26 | 8 | 25 | 65 | 150 |
| I | 40 | 95 | 0 | 1 | 0 | 25 | 62 | 1 |
| J | 40 | 95 | 614 | 25 | 8 | 0 | 3 | 149 |

The peak temperature attained is 289° C., ie 49° C. above the exit temperature. The methanol flow rate in stream I corresponds to about 47.4 te/d. The carbon efficiency in the purge gas treatment stage is 64.6%. The addition of carbon dioxide to the fresh synthesis gas not only enables a greater amount of methanol to be produced in the synthesis loop but also enables an additional 9.6 te/d of methanol to be produced from the purge as compared with Example 5.

I claim:

1. In a method of uprating a methanol synthesis plant, wherein fresh methanol synthesis gas containing hydrogen, carbon oxides, and inert gases is compressed to an elevated synthesis pressure in the range 70–150 bar abs., and fed to a synthesis loop wherein the fresh synthesis gas is mixed with recycle gas, the mixture of compressed synthesis gas and recycle gas is heated and passed over a methanol synthesis catalyst to form a reacted gas stream containing methanol and unreacted gases, the reacted gas stream is cooled to below the dew point of methanol so as to condense methanol which is separated from the reacted gas stream to leave a stream of residual gas, part of which is recycled as the aforesaid recycle gas, and the remainder is discharged from the loop as a purge gas;

the improvement comprising decreasing the delivery pressure of the fresh synthesis gas compressor and increasing the rate at which the fresh synthesis gas is supplied to the synthesis loop without increasing the compression power required, and subjecting the purge gas to a further step of methanol synthesis by heating said purge gas to a synthesis inlet temperature, synthesising methanol from said heated purge gas by passing it over a methanol synthesis catalyst, cooling the reacted purge gas to below the dew point of the methanol therein so as to condense said methanol, separating the condensed methanol and discharging the remainder of the reacted purge gas.

2. A process according to claim 1 wherein at least the final part of the heating of the purge gas to the methanol synthesis inlet temperature comprises heating said purge gas by indirect heat exchange of said purge gas undergoing heating with the purge gas undergoing methanol synthesis, whereby heat is transferred from the purge gas undergoing synthesis to that being heated to the synthesis inlet temperature whereby the purge gas, containing synthesised methanol, leaves the catalyst at a temperature below the maximum temperature achieved by said reacting purge gas during passage over said catalyst.

3. A method according to claim 1 wherein the purge gas is compressed before it is fed to the further synthesis stage.

* * * * *